United States Patent [19]

Marling

[11] 4,292,526
[45] Sep. 29, 1981

[54] ISOTROPICALLY SENSITIVE OPTICAL FILTER EMPLOYING ATOMIC RESONANCE TRANSITIONS

[75] Inventor: John B. Marling, Livermore, Calif.

[73] Assignee: The United States of America as represented by the United States Department of Energy, Washington, D.C.

[21] Appl. No.: 50,860

[22] Filed: Jun. 21, 1979

[51] Int. Cl.$^3$ .............................................. G02B 5/20
[52] U.S. Cl. ...................................... 250/458; 350/312
[58] Field of Search ................... 331/94.5 A, DIG. 1; 250/458; 356/301, 311, 318, 419; 350/1.5, 312; 307/425; 455/619

[56] References Cited

U.S. PATENT DOCUMENTS

| | | | |
|---|---|---|---|
| 3,123,711 | 3/1964 | Fajans | 331/DIG. 1 |
| 3,190,172 | 6/1965 | Langberg | 356/311 |
| 3,204,105 | 8/1965 | Robinson | 356/301 X |
| 3,211,055 | 10/1965 | Andres | 331/DIG. 1 |
| 3,720,882 | 3/1973 | Tang et al. | 307/425 X |
| 3,795,819 | 3/1974 | Harris | 307/425 |
| 3,801,797 | 4/1974 | Harris et al. | 307/425 |

OTHER PUBLICATIONS

Marling et al., *Journal of Applied Physics*, 50(2), Feb. 1979, pp. 610-614.
Marling et al., Lawrence Livermore Laboratory Report Number UCID-17915, available Jan. 9, 1979.

*Primary Examiner*—F. L. Evans
*Attorney, Agent, or Firm*—P. Martin Simpson; Roger S. Gaither; James E. Denny

[57] ABSTRACT

An ultra-high Q isotropically sensitive optical filter or optical detector employing atomic resonance transitions. More specifically, atomic resonance transitions utilized in conjunction with two optical bandpass filters provide an optical detector having a wide field of view ($\sim 2\pi$ steradians) and very narrow acceptance bandwidth approaching 0.01 Å. A light signal to be detected is transmitted through an outer bandpass filter into a resonantly absorbing atomic vapor, the excited atomic vapor then providing a fluorescence signal at a different wavelength which is transmitted through an inner bandpass filter. The outer and inner bandpass filters have no common transmission band, thereby resulting in complete blockage of all optical signals that are not resonantly shifted in wavelength by the intervening atomic vapor. Two embodiments are disclosed, one in which the light signal raises atoms contained in the atomic vapor from the ground state to an excited state from which fluorescence occurs, and the other in which a pump laser is used to raise the atoms in the ground state to a first excited state from which the light signal then is resonantly absorbed, thereby raising the atoms to a second excited state from which fluorescence occurs. A specific application is described in which an optical detector according to the present invention can be used as an underwater detector for light from an optical transmitter which could be located in an orbiting satellite.

19 Claims, 8 Drawing Figures

ISOTROPICALLY SENSITIVE OPTICAL FILTER EMPLOYING ATOMIC RESONANCE TRANSITIONS

BACKGROUND OF THE INVENTION

The invention described herein resulted from Contract W-7405-ENG-48 between the United States Department of Energy and the University of California.

The invention relates to optical filters, and more particularly to optical filters utilizing atomic resonance transitions.

Conventional optical filtering provides narrow bandwidth detectors having small fields of view such as 2.3 degrees for a $\Delta\lambda = 1.0$ Å. There is a need for a narrow spectral bandpass optical detector having a wide field of view in many applications, one being the undersea detection of light from a transmitting laser located above the water surface. A wide field of view is required in such an application because laser light entering the water is projected downwardly in a cone, thus resulting in light irradiating a detector from diverse angles. The present invention provides a detector having an extremely narrow bandwidth on the order of 0.01 A and an extremely wide field of view which could be as high as $2\pi$ steradians.

It is therefore an object of this invention to provide an ultra-high Q, isotropically sensitive optical detector that utilizes atomic resonance transitions of an atomic vapor irradiated by light containing a wavelength to be detected.

Another object of the invention is to detect light only at the fluorescence wavelength of atoms excited by the wavelength to be detected.

A further object of the invention is to provide an optical detector which utilizes an atomic vapor which is raised from a ground state to an excited state by light having a wavelength to be detected.

A still further object of the invention is to utilize an atomic vapor which is raised from a ground state to a first excited state from which it is raised to a second excited state by light having a wavelength to be detected.

Other objects and advantages of the invention will become apparent upon reading the following description.

SUMMARY OF THE INVENTION

The invention provides an ultra-high Q isotropically sensitive optical filter or detector which employs atomic resonance transitions. The detector consists of two spectral bandpass filters, one located on each side of a transparent cell containing an appropriate atomic vapor. One filter passes light at a wavelength to be detected, and the other filter blocks that light, but passes light shifted in wavelength due to resonant transitions in the atomic vapor caused by the light to be detected. Preferably, pass bands of the filters are selected so that no single wavelength is transmitted through both filters. A shift in wavelength after photon absorption by the atomic vapor is caused by radiative decay through intermediate atomic levels and is the basis for the operation of the filter. The number of photons at the shifted wavelength is related to the number of photons at the wavelength to be detected. A detection means, which could be a photomultiplier, for detecting photons at the shifted wavelength is also provided. Thus, the invention provides an optical filter having a wide field of view and a very narrow bandwidth, which can be utilized in a variety of applications.

Two embodiments of the invention are provided, one in which the light to be detected raises the atoms of the atomic vapor from a ground state to a first excited state from which a fluorescence wavelength is generated as the atom returns to the ground state. In a second embodiment, the atoms are raised to a first excited state by a pump laser irradiating the atomic vapor, the atoms as this excited state then being raised to a second excited state by the light to be detected. A fluorescence wavelength from this second excited state is then detected.

The invention is especially useful in a satellite to underwater communication system in which a laser transmitter in the satellite is chosen to have a frequency corresponding to the absorbing frequency of an atomic vapor contained between the two spectral bandpass filters. Since light from the laser transmitter is propagated over a wide angle subsequent to its intersection with the water surface, the wide field of view of the detector provided by the present invention provides a capability for communicating that has heretofore been unachievable with conventional detectors. In addition, the achievable spectral bandwidth approaching 0.01 Å permits much greater rejection of optical noise, such as sunlight. Specific embodiments of the invention are described utilizing potassium, cesium or rubidium as the atomic vapor.

DETAILED DESCRIPTION

Detailed illustrative embodiments of the invention disclosed herein exemplify the invention and are currently considered to be the best embodiments for such purposes. However, it is to be recognized that other atomic vapors and other pump lasers could be utilized in order to provide numerous light filters or detectors according to the teachings of the invention. Accordingly, the specific embodiments disclosed are only representative in providing a basis for the claims which define the scope of the present invention.

As previously explained, the invention provides an optical filter or detector having a wide field of view and a narrow bandwidth, and exhibiting quantum efficiencies exceeding 90% in some embodiments. The detector comprises a first optical filter chosen to transmit a first wavelength $\lambda_1$ and block a second wavelength $\lambda_2$, the first wavelength $\lambda_1$ comprising the light to be detected. A second optical filter is spaced apart from the first optical filter and partially defines a cavity therewith in which an atomic vapor is placed. The second optical filter is chosen to block the first wavelength $\lambda_1$ and transmit the second wavelength $\lambda_2$, the second wavelength $\lambda_2$ comprising a fluorescence wavelength from the atomic vapor. The atomic vapor is raised to either a first excited state by incoming light and fluoresces from that state back to a ground state, or is raised to a first excited state by an irradiating pump laser and then is raised to a second higher state by the incoming light to be detected. Fluorescence from this second higher state back to the ground state creates the second wavelength $\lambda_2$. When the pump laser is utilized, the filter is referred to as an active filter, otherwise it is referred to as a passive filter. In a preferred embodiment, the first and second optical filters are chosen so that there are no common light transmission bands.

Figure 1:
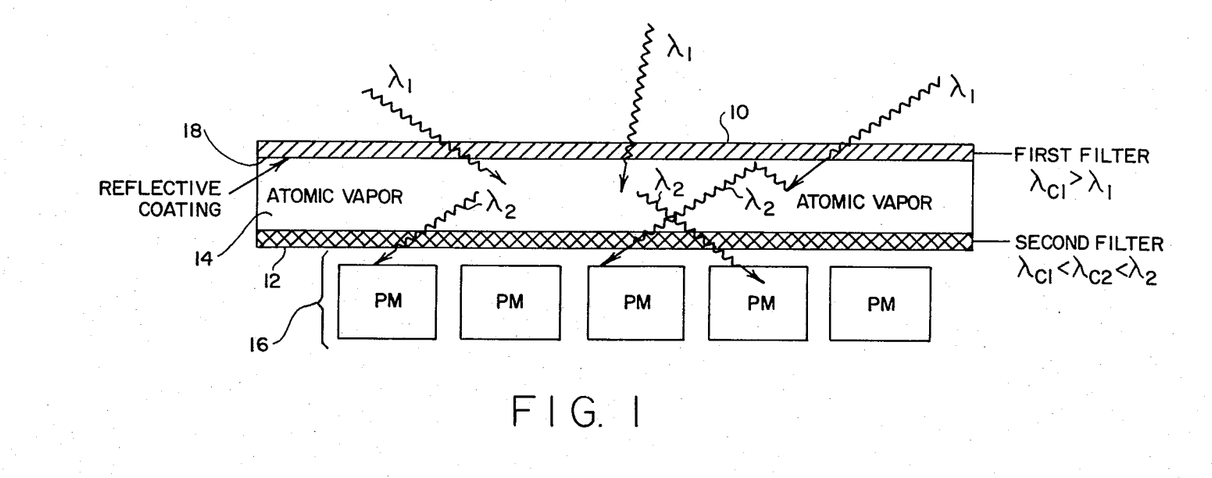
FIG. 1 shows an embodiment of the invention in which atoms in an atomic vapor are raised from a ground state to an excited state by resonant absorption of light to be detected, and then return to the ground state by fluorescing light having a wavelength greater than the wavelength of the light to be detected.

Referring to FIG. 1, a first embodiment showing a passive filter or detector can be seen. A first optical filter 10 is spaced apart from a second optical filter 12, thereby forming a cavity 14 for containment of an atomic vapor. The atomic vapor is chosen so that incoming light to be filtered having a frequency $\lambda_1$ raises atoms in the atomic vapor from a ground state to a first excited state, the thus excited atoms fluorescing to the ground state at a wavelength $\lambda_2$ which is longer than that of $\lambda_1$. In this embodiment, the first optical filter 10 is chosen so that it has a cut-off wavelength $\lambda_{c1}$ greater than $\lambda_1$ thereby allowing light of the wavelength $\lambda_1$ to pass therethrough. The atomic vapor contained within the cavity 14 is raised to a first excited state by absorption of a photon at wavelength $\lambda_1$, and then fluoresces at a wavelength $\lambda_2$ which is longer than that of $\lambda_1$. The second optical filter 12 is chosen so that it has a cut-off wavelength $\lambda_{2c}$ less than the fluorescent wavelength $\lambda_2$ but greater than the cut-off wavelength of the first filter $\lambda_{c1}$. Thus, as one can appreciate, if the atomic vapor is chosen so that it will be raised to an appropriate energy level by photons from light having a wavelength to be detected, and from which fluorescence will take place at a wavelength $\lambda_2$ somewhat removed from $\lambda_1$, then a filter as above-described will prevent any light entering through the first filter 10 from passing through the second filter 12, and only light generated within the cavity 14 at a wavelength $\lambda_2$ will be able to pass through the second filter 12. A bank of photomultipliers 16 are located directly below the second filter 12, the photomultipliers being chosen to be responsive to the fluorescence wavelength $\lambda_2$. A reflective coating 18 which transmits at wavelength $\lambda_1$, but reflects at wavelength $\lambda_2$ is provided on the side of the first optical filter 10 closest to the cavity 14 in order to prevent absorption of the various light components within the cavity 14. Doppler broadening in the wavelength-shifting of the atomic vapor determines the operating bandwidth of the detector, and is approximately 0.01 Å per hyperfine line component at optical wavelengths. The atomic vapor contained between the two optical filters 10 and 12 is isotropically sensitive to incoming radiation, and its effective solid angular sensitivity is limited only by the available fractional transparent surface area of the first filter 10. The time response of the detector is determined by the natural, as well as radiative trapping lifetimes of the atomic levels employed in the wavelength shifting, these lifetimes typically being between 0.1 and 10 microseconds. Also as will be understood by those familiar with optical filters, absolute cut-off frequencies are rarely obtained. Thus it is assumed that a filter is in a cut-off region when more than 85% of incident light is blocked.

Examples of passive type filters in which transition levels are given for potassium, cesium and rubidium are shown in Table 1.

TABLE 1

| ATOMIC VAPOR | TRANSITION | ABSORPTION WAVELENGTH $\lambda_1$ | FLUORESCENCE WAVELENGTH $\lambda_2$ | DOPPLER WIDTH AT $\lambda_1$ |
|---|---|---|---|---|
| POTASSIUM | 4s-3d$^2$D$_{5/2}$ | 4641.88Å | 7664Å | 0.0135Å |
| POTASSIUM | 4s-3d$^2$D$_{3/2}$ | 4642.37Å | 7698Å | 0.0135Å |
| CESIUM | 6s-7p$^2$P$_{3/2}$ | 4555.28Å | 8521Å | 0.022A |
| CESIUM | 6s-7p$^2$P$_{\frac{1}{2}}$ | 4593.17Å | 8943Å | 0.022Å |
| RUBIDIUM | 5s-4d$^2$D$_{5/2}$ | 5165.18Å | | 0.0095Å |
| RUBIDIUM | 5s-4d$^2$D$_{3/2}$ | 5165.06Å | 7800Å | 0.0095Å |
| RUBIDIUM | 5s-6p$^2$P$_{\frac{1}{2}}$ | 4215.52Å | 7947Å | 0.0078Å |
| RUBIDIUM | 5s-6p$^2$P$_{3/2}$ | 4201.79Å | | 0.0078Å |

Figure 2:
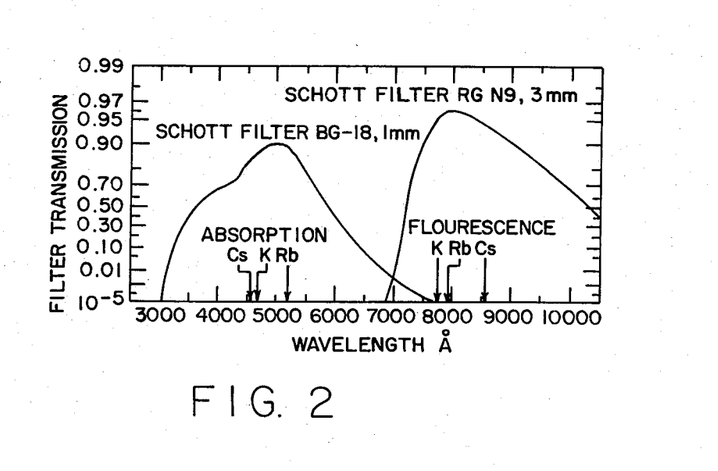
FIG. 2 shows filters and their transmission characteristics which can be used in the embodiment of FIG. 1.

As can be seen, all of these transition levels occur from the ground state to a higher state. For example, referring to potassium, an absorption wavelength with a Doppler width of 0.0135 Å occurs for transitions from the 4s level to the 3d$^2$D$_{3/2}$ at 4642.37 Å. From both of these 3d levels, fluorescence occurs at 7664 Å and 7698 Å. Thus, if a cut-off frequency for the first optical filter 10 is greater than 4650 Å and a cut-off frequency for the second optical filter 12 is greater than that of the first filter 10 and less than 7,500 Å, then no wavelength entering the cavity 14 through the first filter 10 can pass through the second filter 12, and all light within the pass band of the second filter 12 is created as a result of the fluorescence of the atomic vapor. As can be seen, the same relationships occur for cesium and rubidium. FIG. 2 shows filters and their transmission characteristics which could be utilized in a passive detector. As can be seen, the first filter 10 comprises a Schott filter BG-18 and the second filter 12 comprises a Schott filter RG N9. Other atomic vapors which could be utilized include magnesium which absorbs light at 4571.10 Å and strontium at 4607.33 Å.

Referring to Table 2, some of the parameters associated with the various atomic vapors described above can be seen.

TABLE 2

|  | VAPOR TEMPERATURE | QUANTUM EFFICIENCY | PM QUANTUM EFFICIENCY |
|---|---|---|---|
| POTASSIUM | 320° C. | 100% | 20% |
| CESIUM | 95° C. | ≧95% | 16% |
| RUBIDIUM |  |  |  |
| 5165.18Å or 5165.06Å | 295° C. | 100% | 20% |
| 4215.52Å or 4201.79Å | 100° C. | >95% | 20% |

Quantum efficiency is defined as the number of photons generated at the fluorescence wavelength $\lambda_2$ divided by the number of photons absorbed at the absorption wavelength $\lambda_1$. As can be seen by referring to Table 2, all of the passive detectors have high quantum efficiencies, the potassium and some of the rubidium transitions being at substantially 100%. The vapor temperature for potassium is one of the highest, however, it being 320° C. The photomultiplier quantum efficiencies are considerably less as can be seen, most being about 20%, typical for GaAs-type photomultipliers. Overall quantum efficiency for the various detectors can be derived by multiplying the quantum efficiency of the absorption and fluorescence process by the quantum efficiency of the photomultiplier. As previously stated, one of the big advantages of the type of detector above-described is derived from isotropic absorption of incident light by the atomic vapor. If the incoming filter is angle insensitive, then detector fields-of-view are only limited by the solid angle subtended by the photomultiplier array. As the quantum efficiency of photomultipliers is improved, or more optimum photomultipliers are utilized, the overall quantum efficiency of the detector can be increased.

Figure 3:
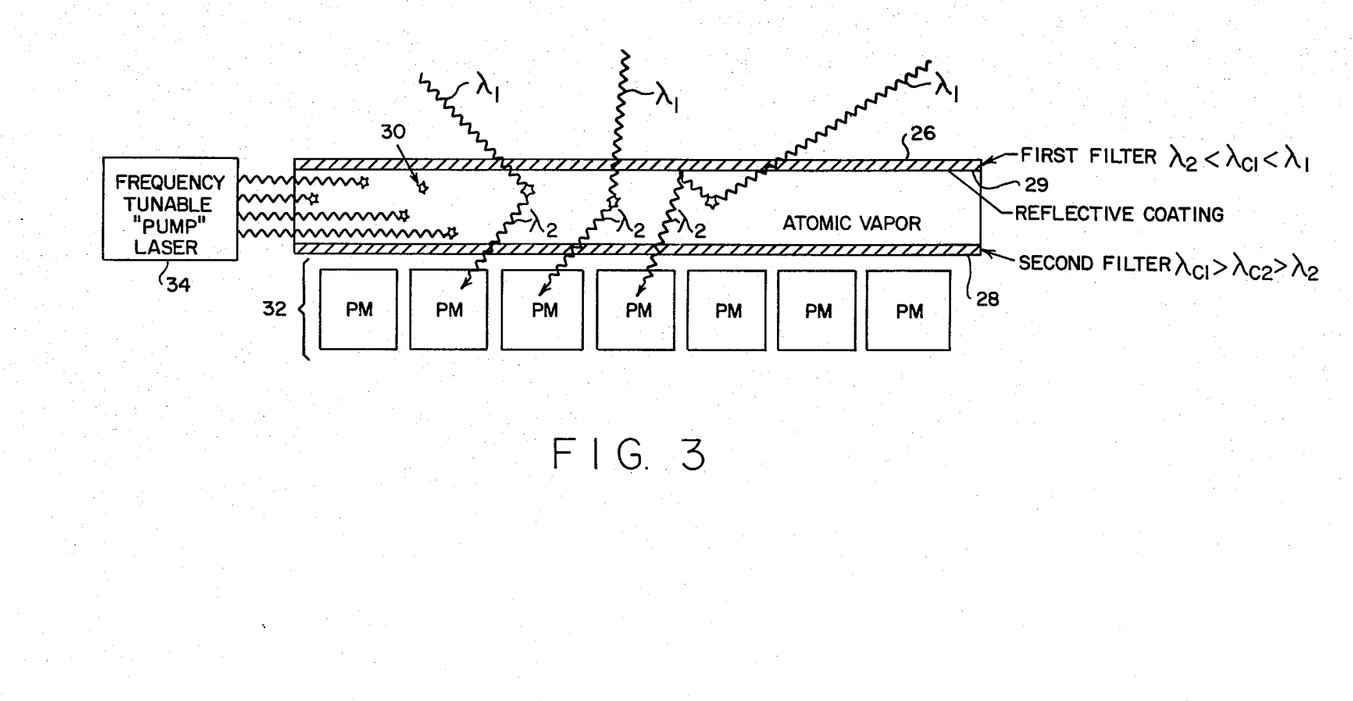
FIG. 3 is a further embodiment of the invention in which the atoms in an atomic vapor are raised to a first excited state by a pump laser, and then raised to a second higher excited state by light to be detected, and then fluorescing from the second higher state to a ground state at a wavelength shorter than the wavelength of the light to be detected.

A second embodiment of the invention utilizes a pump laser which raises the atomic vapor between the two filters to a first higher state. The incoming light to be detected then raises the vapor from the first higher state to a second higher state from which fluorescence to the ground state occurs. Referring to FIG. 3, incoming radiation $\lambda_1$ to be detected is converted to a fluorescence radiation $\lambda_2$. In typical detectors utilizing a pump laser, the fluorescence wavelength $\lambda_2$ is shorter than the wavelength $\lambda_1$ to be detected. When this wavelength relationship exists, a first optical filter 26 has a cut-off wavelength $\lambda_{c1}$ which is less than the wavelength $\lambda_1$ to be detected and greater than the fluorescence wavelength $\lambda_2$. A second optical filter 28 is provided which has a cut-off wavelength $\lambda_{c2}$ less than the cut-off wavelength $\lambda_{c1}$ of the first filter 26 and greater than the fluorescence wavelength $\lambda_2$. Thus, any light which can pass through the first filter 26 has a wavelength greater than $\lambda_{c1}$ and therefore is blocked by the second filter 28 which has cut-off wavelength $\lambda_{c2}$ less than the cut-off wavelenth $\lambda_{c1}$ of the first filter 26. A reflective coating 29 for $\lambda_2$ wavelengths is provided on the inner surface of the first filter 26. An appropriate atomic vapor is contained within a cavity 30 defined by the first and second filters 26 and 28 respectively. As in the first embodiment, a photomultiplier array 32 is provided, the specific photomultiplier being chosen to maximize detection of photons at the fluorescence wavelength $\lambda_2$. A frequency tunable pump laser 34, which could be a dye laser, is provided to irradiate the atomic vapor thereby raising the atoms contained therein from a ground state to a first excited state which will be receptive to photons at the wavelength $\lambda_1$ to be detected.

An example of an active detector according to the second embodiment utilizes potassium as the atomic vapor. The pump laser is a tunable dye laser radiating at a wavelength of 7698.98 Å. This optically pumps the potassium vapor from the 4s level to the $4p^2P_{\frac{1}{2}}$ level. A second transition from the 4p level to the 8s level can be achieved by irradiating the thus excited potassium vapor with a wavelength of 5323.28 Å obtained from a frequency doubled neodymium-YAG (Nd-YAG) laser transmitter. From this second transition level, fluorescence occurs from the potassium 5p to 4s level at 4045 Å with a 5% quantum efficiency. Again, as in the first embodiment, the first and second optical filters 26 and 28 are chosen so that all incoming light passed by the first filter 26 is blocked by the second filter 28 and that light at the fluorescence wavelength of 4045 Å is blocked by the first filter 26 and passed by the second filter 28. Thus, only transitions occurring as a result of incoming light at 5323.28 Å is detected by the photomultiplier array 32. Thus, the pump laser 34 irradiates the atomic vapor with resonantly matched laser radiation to excite the atomic vapor so that it will then be able to effectively absorb the incident radiation to be detected. Other possible transitions which can be detected using pump laser activation include lithium at 4603 Å (2p-4d), lithium at 4972 Å (2p-4s), sodium at 4751 Å (3p-7s), sodium at 5151 Å (3p-6s), sodium at 4668 Å (3p-6d), sodium at 4981 Å (3p-5d) and magnesium at 4730 Å (3p-6s). As previously explained, the transition at 5323.28 Å for potassium is accessible by tuning a frequency doubled Nd-YAG laser at 1.06 microns. As will be explained below, surface to underwater communication is possible using a Nd-YAG laser and a detector according to the present invention.

Figure 4:
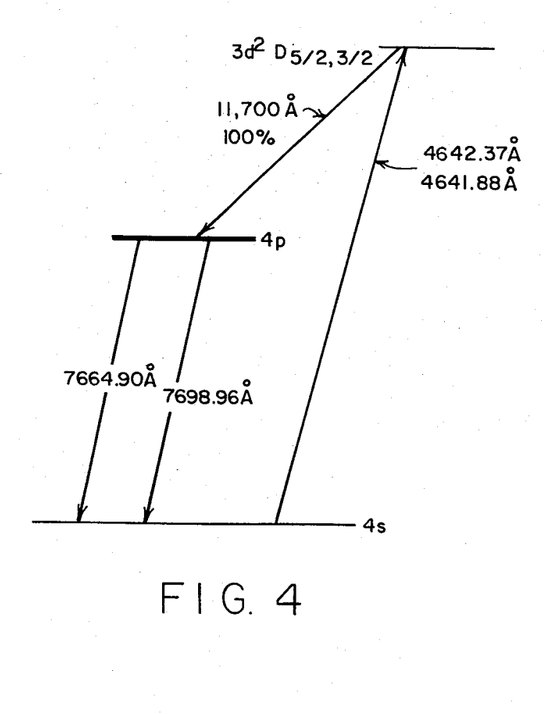
FIG. 4 is an energy level diagram for potassium in which light to be detected raises potassium atoms to a first excited state.
Figure 5:
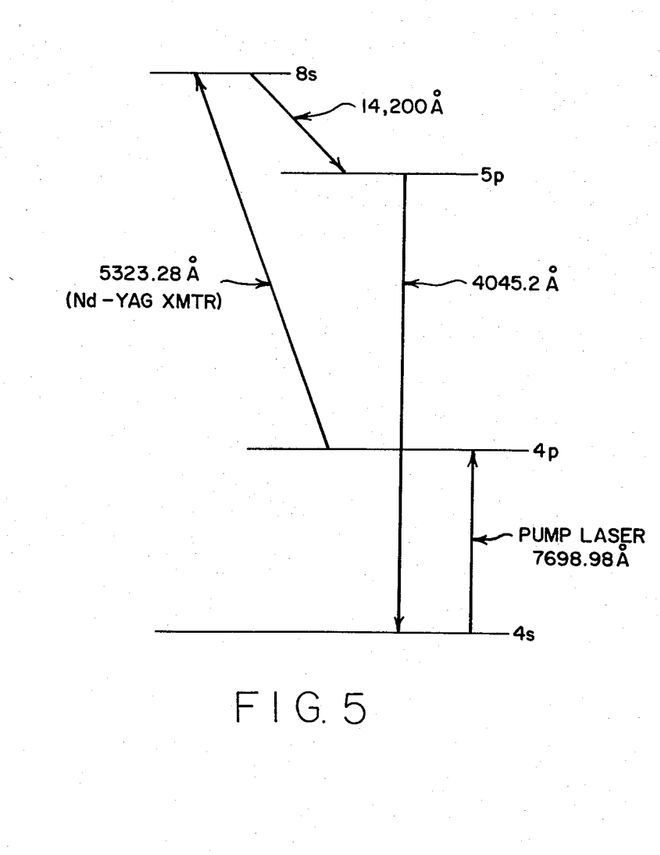
FIG. 5 is an energy level diagram for potassium in which potassium atoms are raised to a first excited state by a pump laser and then raised to a second higher state by light to be detected.

Transitions for a passive detector utilizing potassium as the atomic vapor can be seen in FIG. 4. Incoming radiation to be detected at 4642.37 Å or 4641.88 Å raises potassium atoms comprising the atomic vapor from the ground state to the 3d level. From the 3d level, fluorescence occurs at 11,700 Å to the 4p level from which fluorescence back to the ground state 4s occurs at two wavelengths 7664.90 Å and 7698.96 Å. Thus, as one can appreciate, a laser transmitter radiating at one of the above wavelengths can be detected at the two fluorescence wavelengths by a detector provided by the invention. FIG. 5 shows transitions for an active detector also using potassium as the atomic vapor. Here the pump laser raises the potassium atoms from the 4s to the 4p level by irradiating the atomic vapor at 7698.98 Å, this wavelength being obtainable from a tunable dye laser. Light from a frequency-doubled Nd-YAG laser transmitter operating at 5323.28 Å further raises the potassium atoms from the 4p level to the 8s level from which fluorescence occurs at 14,200 Å to the 5p level and then to the ground state at 4045.2 Å.

One specific application for a detector provided by the invention is as the underwater receiver of an airborne to underwater optical communication system operable in the presence of solar illumination. Such a detector requires a very narrow bandwidth to eliminate solar-induced noise, a wide solid angle of reception, and high sensitivity. Several problems must be surmounted in order to effectively communicate underwater, the first of which is signal transmission through the ocean. Because of ocean properties, the electromagnetic wave frequency best suited to penetrating the ocean to depths of hundreds of meters in the presence of ambient solar noise is that of blue-green light in the spectral range of 4,000 Å to 5,500 Å. Since the sun produces a major portion of its light in the 4,000 to 5,500 Å spectral region, it constitutes a large source of noise. As a result, a very narrow bandwidth of signal transmission and reception must be used in order to reduce in-band solar background noise to acceptably low levels. In addition, the ocean also absorbs strongly, even at optimal transmission wavelengths. In the 4,000 Å to 5,500 Å spectral region, the ocean absorbs roughly exponentially with depth, the l/e absorption lengths varying between 10 and 50 meters. This means a practical underwater optical receiver must have excellent sensitivity. Scattering in the atmosphere and ocean is also significant. Light after transmission through the ocean will be scattered into a downward-directed cone having an opening angle of tens of degrees, thereby resulting in the optical signal incident on the underwater detector being from a large solid angle. An underwater detector should therefore be capable of receiving from essentially all upward-oriented directions. Thus, an ideal underwater optical detector should have a small bandwidth of reception, high sensitivity, and a large angle of reception. An optical detector according to the present invention meets all of these requirements. A detector 38 which can be utilized in an air to underwater communication system 13 is shown in FIG. 6.

Figure 6:
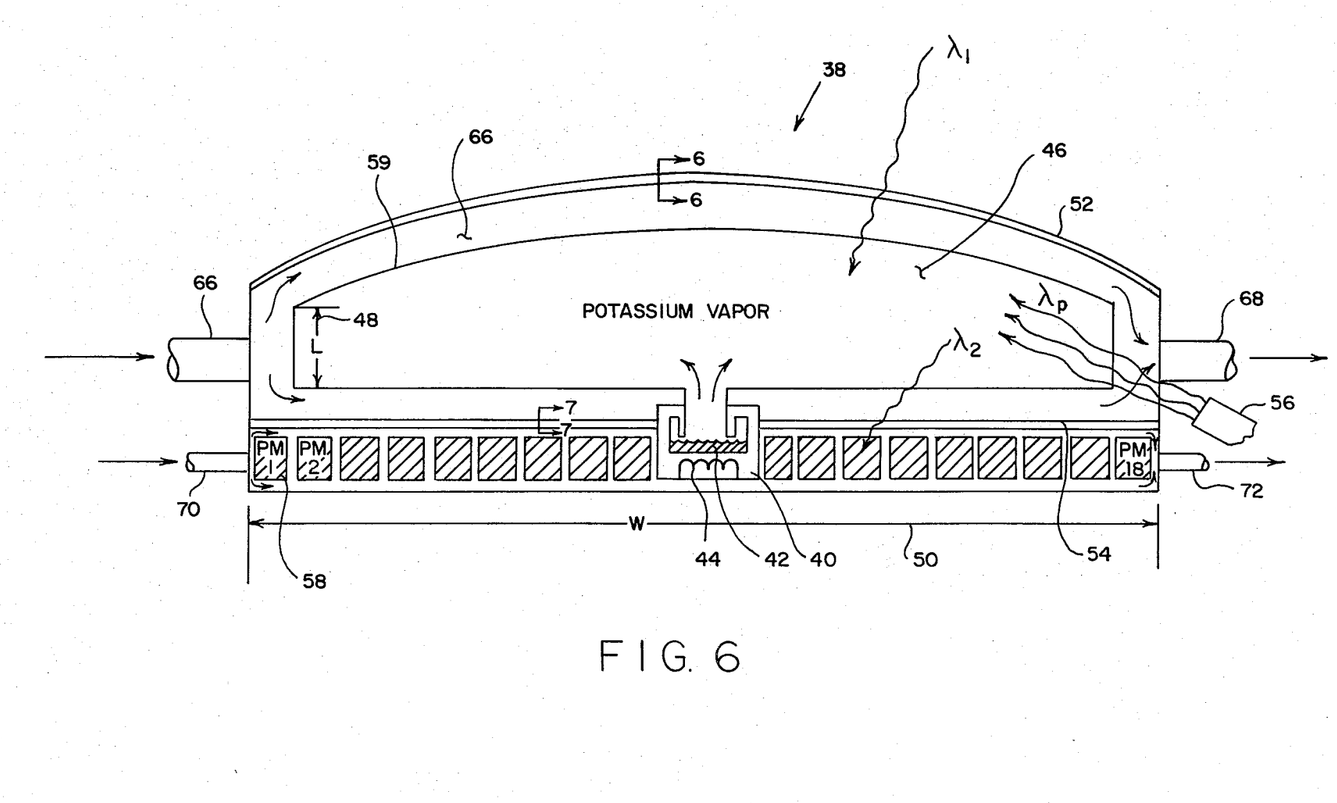
FIG. 6 shows an optical detector constructed according to the invention for use in a satellite to underwater communication system.

Referring to FIG. 6, an oven 40 contains potassium 42 which is heated by heating coils 44. The potassium 42 temperature is maintained at approximately 120° C. in order to provide potassium vapor of the proper density in a vapor cavity 46. An important parameter in sizing the detector 38 is insuring that the dimension L is at least a certain minimum length. The width W shown at 50 can be of any dimension, even shorter than L as long as side wall reflecting is high. However, L must be at least several ($\sim 3$) mean-free absorption paths. Unless photons travel through several mean-free absorption paths while in the atomic vapor, they will not be absorbed and thus detected with high efficiency. The mean-free path 1 for photon absorption is determined by $1 = 1/n\sigma$; where $\sigma$ is the cross section for absorption at a given wavelength and n is the number density of the atomic vapor atoms. Both of these parameters can be readily determined for any particular atomic vapor. The density of the atomic vapor atoms should be kept as small as possible to minimize collisional effects. For the detector shown in FIG. 6, L should be at least 10 cm for a potassium temperature of 120° C. An active detector has been chosen for illustrative purposes in order to utilize a space-qualified Nd-YAG laser having a frequency-doubled output of 5,323.28 Å. Although overall quantum efficiencies for an active detector utilizing the 4p-8s transition for absorption of the wavelength to be detected are lower than those for a passive detector, the current availability of a space-qualified Nd-YAG laser makes this a practical embodiment for underwater communication. Referring again to FIG. 6, a first optical filter 52 is chosen to block light having wavelengths shorter than 5,000 Å. A second optical filter 54 is provided, this filter 54 passing wavelengths below 4,200 Å, 4045 Å being the fluorescence wavelength $\lambda_2$ as previously described. A pump laser 56, which is a tunable dye laser, is provided to irradiate the potassium with light having a wavelength $\lambda_p$ of 7698.90 Å. A photomultiplier array 58 is also provided, the array 58 consisting of a plurality of photomultipliers sensitive to 4045 Å. Again, the cut-off wavelengths of the first and second optical filters 52 and 54, respectively, are chosen so that any light entering through the first optical filter 52 is blocked by the second optical filter 54. A potential problem in the above-described detector is a fogging of the first and second optical filter inner surfaces by alkali metal deposition thereon. This problem can be obviated by maintaining the temperature of the outside surface of a glass wall 59 defining the vapor cavity 46 at least slightly higher than that of the oven 40 containing the liquid potassium 42, thereby guaranteeing that the potassium vapor will condense only in the oven 40. However, the temperature of the glass wall 59 should not be too high in order to avoid potassium atoms implanting themselves in the glass, thereby decreasing its transmissivity. In order to maintain the proper temperature, the optical filters 52 and 54 are spaced apart from the glass wall 59 in order to form a heating chamber 66. A heating fluid which could be hot air, enters the heating chamber 66 through an entrance duct 67, the heating fluid being transparent to both $\lambda_1$ and $\lambda_2$ wavelengths. The heating fluid is chosen to be approximately 50° C. higher than the temperature of the oven 40, thereby resulting in the fluid being at approximately 170° C. This fluid flows through the heating chamber 66 and exists through an exit duct 68. Cooling for the photomultiplier array 58 is provided by a coolant material at a temperature less than $-40°$ C. The coolant enters through a coolant entrance duct 70 and exits through a coolant exit duct 72. This coolant cools the photomultiplier array in order to increase its efficiency in detecting photons at the fluorescence wavelength $\lambda_2$. It should be noted that commercially available photomultipliers have quantum efficiencies of 30% at 4,000 Å.

Figure 7:
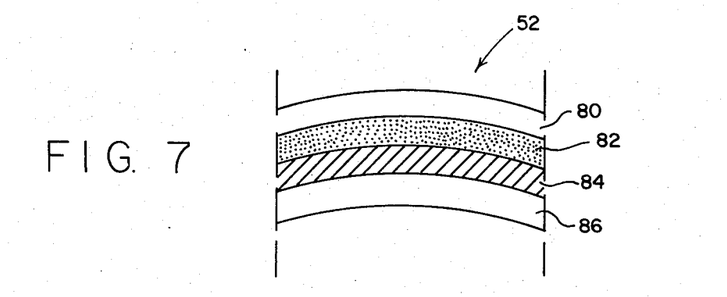
FIG. 7 is a cross sectional view taken along line 6—6 of FIG. 6.
Figure 8:
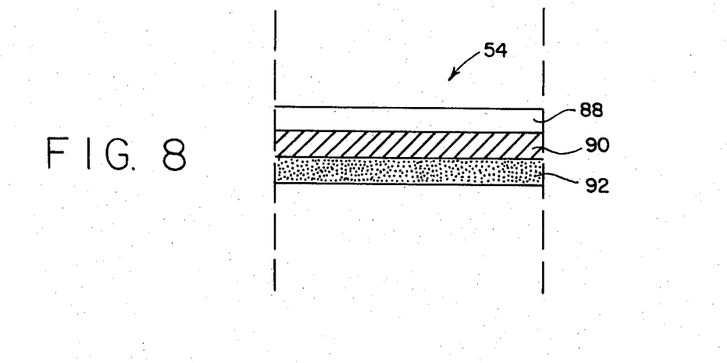
FIG. 8 is a cross sectional view taken along line 7—7 of FIG. 6.

Referring to FIG. 7, a cross section of the first optical filter 52 is shown. The filter 52 comprises a glass or plastic transparent portion 80 which provides strength against ocean water pressure, a glass dye filter 82 which blocks the fluorescence wavelength $\lambda_2$ and transmits the wavelength $\lambda_1$ to be detected. A dielectric filter 84 which could be a multi-layer dielectric coating on filter 82, is also supplied, this filter transmitting $\lambda_1$ and reflecting $\lambda_2$ thus insuring the light at the fluorescence wavelength $\lambda_2$ cannot pass outwardly through the first optical filter 52. A final layer of glass 86 is supplied which acts as a heat shield. A cross section of the second optical filter 54 is shown in FIG. 8. This filter comprises a glass shield 88, a dielectric filter 90, which could be a multi-layer dielectric coating on shield 88, which transmits $\lambda_2$ and reflects $\lambda_1$, and a glass dye filter 92 which blocks $\lambda_1$ and also transmits $\lambda_2$. The two filters 82 and 92 are glass filters dyed "en masse", and have spectral properties which are effectively independent of incident angle. In operation, the quantum efficiency of the conversion of light entering at 5323.28 Å and leaving the 4045 Å is approximately 7%. This combined with a quantum efficiency of the photomultiplier array of 30% gives an overall quantum efficiency of 2.1% for the detector. Again, even though this quantum efficiency is low with respect to that obtainable with many of the passive detectors previously described, its use in conjunction with a Nd-YAG laser already developed for space transmission systems provides an especially promising means for providing a satellite to underwater communication system. However, as other laser transmitters become available, many of the other wavelengths described above can be also utilized.

Thus, it should be apparent from the above description that an optical detector has been disclosed which has a wide field of view and a very narrow acceptance bandwidth. Light to be detected passes through an outer filter into a resonantly absorbing atomic vapor, which in turn fluoresces at another wavelength which is transmitted through an inner filter and subsequently detected. The outer and inner filters are chosen to have no common transmission band, thereby resulting in complete blockage of all optical signals that are not resonantly shifted in wavelength by the atomic vapor. Two embodiments have been disclosed, one being a passive detector in which the incoming light excites the atomic vapor from an initial ground state, and the other an active detector in which a pump laser raises the atomic vapor from a ground state to a first excited state from which it is raised to a second higher state by the incoming light to be detected.

What is claimed is:

1. A method for detecting light at a first wavelength $\lambda_1$ comprising the steps of:
    providing an atomic vapor having atoms at a first energy level and capable of absorbing light at said first wavelength $\lambda_1$ and, having absorbed said light at said first wavelength $\lambda_1$, fluorescing light at a second wavelength $\lambda_2$;
    providing a first optical filter chosen to transmit said first wavelength $\lambda_1$ and block said second wavelength $\lambda_2$;
    providing a second optical filter spaced apart from said first optical filter and partially defining a cavity therewith for containment of said atomic vapor, said second optical filter being chosen to block said first wavelenght $\lambda_1$ and transmit said second wavelength $\lambda_2$; and
    subjecting said atomic vapor to irradiation by light at said first wavelength $\lambda_1$ thereby causing said atoms having said first energy level to be excited to a second higher energy level by absorption of light at a narrow band wavelength centered at $\lambda_1$, said excited atoms then fluorescing at a fluorescence wavelength $\lambda_2$ to a third energy level lower than said second energy level whereby light at said first wavelength $\lambda_1$ passing through said first optical filter is converted to light having said second wavelength $\lambda_2$ passing through said second optical filter.

2. The method of claim 1 wherein said first optical filter and said second optical filter are chosen to have no common light transmission bands.

3. The method of claim 1 further comprising the step of detecting light at said second wavelength $\lambda_2$ after having passed through said second optical filter.

4. The method of claim 1 wherein said first energy level is not a ground level, said providing an atomic vapor step comprises the step of exciting atoms in said atomic vapor to said first energy level.

5. The method of claim 4 wherein said step of exciting atoms comprises irradiating said atomic vapor with light from a pump laser having a third wavelength $\lambda_3$.

6. The method of claim 5 wherein said atomic vapor is an alkali metal vapor.

7. The method of claim 6 wherein said alkali metal vapor is potassium vapor, $\lambda_3$ is 7698.98 Å, $\lambda_1$ is 5323.28 Å and $\lambda_2 = 4045$ Å.

8. The method of claim 1 wherein said first energy level is a ground level and said atomic vapor is an alkali metal vapor.

9. The method of claim 8 wherein said alkali metal vapor is potassium vapor, $\lambda_1$ is between 4641 Å and 4643 Å and $\lambda_2$ is between 7699 Å and 7664 Å.

10. The method of claim 8 wherein said alkali metal vapor is cesium vapor, $\lambda_1$ is between 4555 Å and 4594 Å, and $\lambda_2$ is between 8520 Å and 8944 Å.

11. The method of claim 8 wherein said alkali metal vapor is rubidium vapor, $\lambda_1$ is between 5165 Å and 5166 Å, and $\lambda_2$ is between 7800 Å and 7948 Å.

12. The method of claim 8 wherein said alkali metal vapor is rubidium vapor, $\lambda_1$ is between 4201 Å and 4216 Å, and $\lambda_2$ is between 7800 Å and 7948 Å.

13. A method for detecting light having a wavelength $\lambda_1$ comprising the steps of:
    providing a first optical filter having an optical transmission wavelength less than a predetermined first cutoff wavelength $\lambda_{c1}$, where $\lambda_1 < \lambda_{c1}$;
    providing a second optical filter spaced apart from said first optical filter and having an optical transmission wavelength greater than a second cutoff wavelength $\lambda_{c2}$ and where $\lambda_{c2} > \lambda_{c1}$;
    providing an atomic vapor having a ground state from which said vapor can be raised to an excited state by absorption of light at a narrow band wavelength centered at $\lambda_1$ where $\lambda_1 < \lambda_{c1} < \lambda_{c2}$, and which will exhibit a fluorescent transition from said excited state to the ground state by emission of light at a fluorescence wavelength $\lambda_2$ where $\lambda_2 > \lambda_{c2}$;
    positioning said atomic vapor between and adjacent to said first and second optical filters;
    irradiating said atomic vapor through said first optical filter with said light to be detected; and
    detecting light at said fluorescence wavelength $\lambda_2$ after having passed through said second optical filter.

14. A method for detecting light having a wavelength $\lambda_1$ comprising the steps of:
    providing a first optical filter having an optical transmission wavelength greater than a first cutoff wavelength $\lambda_{c1}$, where $\lambda_1 > \lambda_{c1}$;
    providing a second optical filter spaced apart from said first optical filter and having an optical transmission wavelength less than a second cutoff wavelength $\lambda_{c2}$ where $\lambda_{c2} < \lambda_{c1}$;
    providing an atomic vapor positioned between and adjacent to said first and second optical filters;
    pumping said atomic vapor to a first excited state from which light can be absorbed at a narrow band wavelength centered at $\lambda_1$ thereby raising said atomic vapor to a second excited state, said vapor at said second excited state exhibiting a fluorescence transition to the ground state by emission of light at a fluorescence wavelength $\lambda_2$ where $\lambda_2 < \lambda_1$, whereby light at the absorption wavelength $\lambda_1$ incident on said first optical filter is transformed to light at the fluorescence wavelength $\lambda_2$ and emitted through said second optical filter; and
    detecting light at said fluorescence wavelength $\lambda_2$ emitted through said second optical filter.

15. A filter for detecting light at a first wavelength $\lambda_1$ comprising:
    an atomic vapor having atoms at a first energy level, said atoms being capable of absorbing light at said first wavelength $\lambda_1$ and, having absorbed said light at said first wavelength $\lambda_1$, fluorescing light at a second wavelength $\lambda_2$;

a first optical filter chosen to transmit light at said first wavelength $\lambda_1$ and block light at said second wavelength $\lambda_2$; and a second optical filter spaced apart from said first optical filter and partially defining a cavity therewith for containment of said atomic vapor, said second optical filter being chosen to block said first wavelength $\lambda_1$ and transmit said second wavelength $\lambda_2$ whereby irradiation of said atomic vapor by light having said first wavelength $\lambda_1$ and passing through said first optical filter causes said atoms having said first energy level to be excited to a second higher energy level by absorption of light at a narrow band wavelength centered at $\lambda_1$, said excited atoms then fluorescing to a third energy level lower than said second energy level at a fluorescence wavelength $\lambda_2$ thereby resulting in light at said first wavelength $\lambda_1$ passing through said first optical filter being transformed to light having said second wavelength $\lambda_2$ and passing through said second optical filter.

16. The filter of claim 15 wherein said first and second optical filters have no common light transmission bands.

17. The filter of claim 15 further comprising means for detecting light at said second wavelength $\lambda_2$ having passed through said second optical filter.

18. The filter of claim 15 wherein said first and third energy levels are ground levels.

19. The filter of claim 15 wherein said first energy level is not a ground level, further comprising means for exciting atoms in said atomic vapor from a ground state to said first energy level.

* * * * *